(12) United States Patent
Pei et al.

(10) Patent No.: US 12,282,001 B2
(45) Date of Patent: Apr. 22, 2025

(54) SYSTEMS, DEVICES, AND METHODS FOR ELECTROCHEMICAL WATER ANALYSIS

(71) Applicant: Queen's University at Kingston, Kingston (CA)

(72) Inventors: Yu Pei, Kingston (CA); Zhe She, Kingston (CA); Sarah Jane Odessa Payne, Kingston (CA)

(73) Assignee: Queen's University at Kingston, Kingston (CA)

( * ) Notice: Subject to any disclaimer, the term of this patent is extended or adjusted under 35 U.S.C. 154(b) by 319 days.

(21) Appl. No.: 18/115,344

(22) Filed: Feb. 28, 2023

(65) Prior Publication Data
US 2023/0280309 A1 Sep. 7, 2023

Related U.S. Application Data

(60) Provisional application No. 63/315,192, filed on Mar. 1, 2022.

(51) Int. Cl.
*G01N 33/18* (2006.01)
*G01N 29/036* (2006.01)
*G01N 29/24* (2006.01)

(52) U.S. Cl.
CPC ....... *G01N 29/036* (2013.01); *G01N 29/2443* (2013.01); *G01N 33/18* (2013.01); *G01N 2291/022* (2013.01)

(58) Field of Classification Search
None
See application file for complete search history.

(56) References Cited

U.S. PATENT DOCUMENTS

| | | | |
|---|---|---|---|
| 2004/0126814 A1* | 7/2004 | Singh | C08F 8/00 435/7.1 |
| 2005/0003560 A1* | 1/2005 | Zeng | G01N 33/54373 436/527 |
| 2017/0276643 A1* | 9/2017 | Chow | G01N 27/423 |

OTHER PUBLICATIONS

Špičák, P., Sedlaříková, M., Zatloukal, M. et al. Preparation and properties of manganese dioxide studied by QCM. J Solid State Electrochem 14, 2139-2144 (2010). https://doi.org/10.1007/s10008-010-1198-2 (Year: 2010).*

Validation of Electrochemical Sensor for Determination of Manganese in Drinking Water; Elena Boselli, Zhizhen Wu, Alexa Friedman, Birgit Claus Henn, and Ian Papautsky; Environmental Science & Technology 2021 55 (11), 7501-7509 (Year: 2021).*

(Continued)

*Primary Examiner* — Alexander A Mercado
(74) *Attorney, Agent, or Firm* — Stephen J. Scribner

(57) ABSTRACT

Methods and apparatus for electrochemical analysis of water include acid cleaning a quartz crystal microbalance (QCM), stabilizing a QCM in analyte solution, and analyzing the solution by chronoamperometry and measuring a frequency shift of the QCM. The method may further include cleaning the QCM in an acid solution prior to stabilizing the QCM in analyte solution. The apparatus may provide at least semi-automated electrochemical analysis of water including determining a concentration of an analyte in a water sample, and communicating the concentration of the analyte over a network. The analyte may be manganese.

20 Claims, 14 Drawing Sheets

(56) References Cited

OTHER PUBLICATIONS

Health Canada, Guidelines for Canadian Drinking Water Quality: Guideline Technical Document-Manganese. Health Canada: Water and Air Quality Bureau, Healthy Environments and Consumer Safety Branch, Health Canada, Ottawa, Ontario, 2019.

Kang, W., et al. "Determination of manganese by cathodic stripping voltammetry on a microfabricated platinum thin-film electrode", Electroanalysis 2017, 29 (3), pp. 686-695.

Toronto Drinking Water Analysis Summary, 2020 (https://www toronto.ca/wp-content/uploads/2021/05/8e4a-DS21-0106-DrinkingWaterAnalysis2020-AODA.pdf).

World Health Organization, Manganese in Drinking Water—Background document for development of WHO Guidelines for Drinking-water Quality—Version for public review. WHO. World Health Organization, Geneva, Switzerland, 2020.

Berg, K. E., et al., "Manganese Detection Using Stencil-printed Carbon Ink Electrodes on Transparency Film", Electroanalysis, 28 (4), pp. 679-684, (2016).

Owen, M. P., et al., "An electrochemical quartz crystal microbalance study into the deposition of manganese dioxide", Electrochimica acta, 52 (14), pp. 4630-4639, (2007).

Standard Methods for the Examination of Water and Wastewater, 23rd Edition. American Public Health Association, Water Environment Federation, American Water Works Association, 2017, (Chapters 3010, 3020, 3030, 3111, 3113, 3120, 3125, 3500).

\* cited by examiner

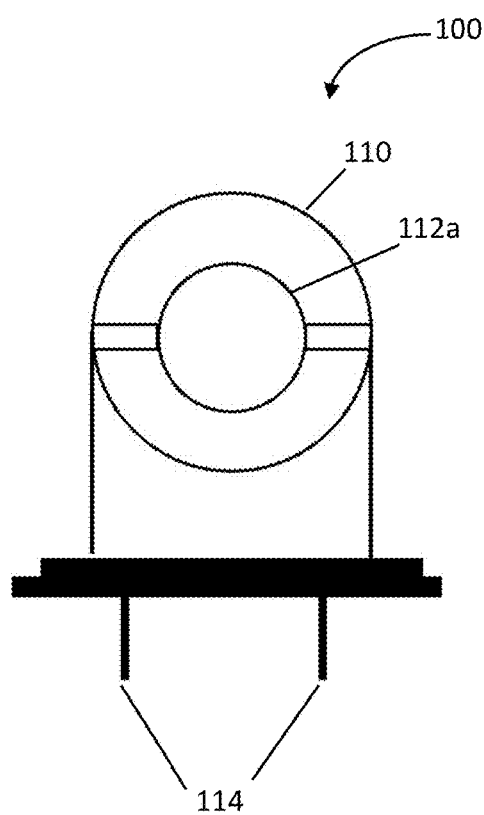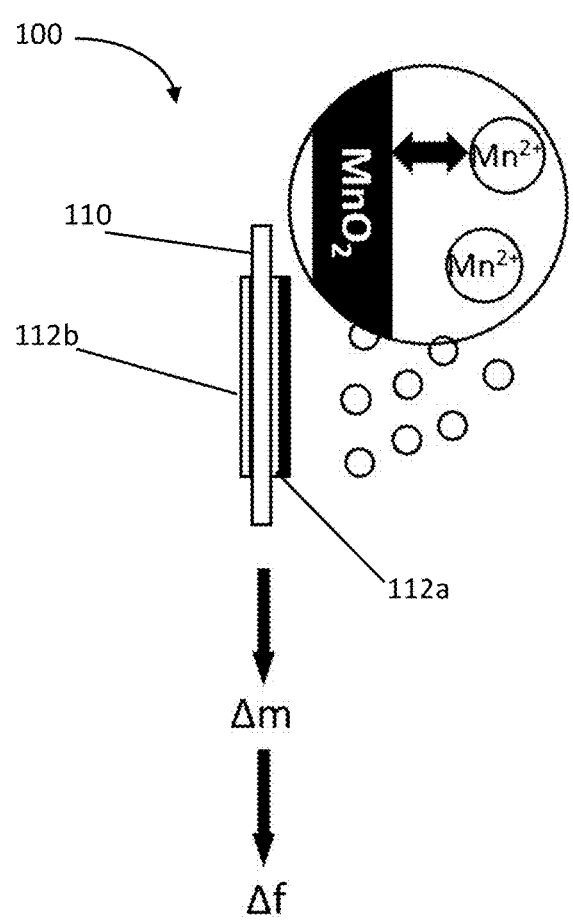
FIG. 1A
FIG. 1B
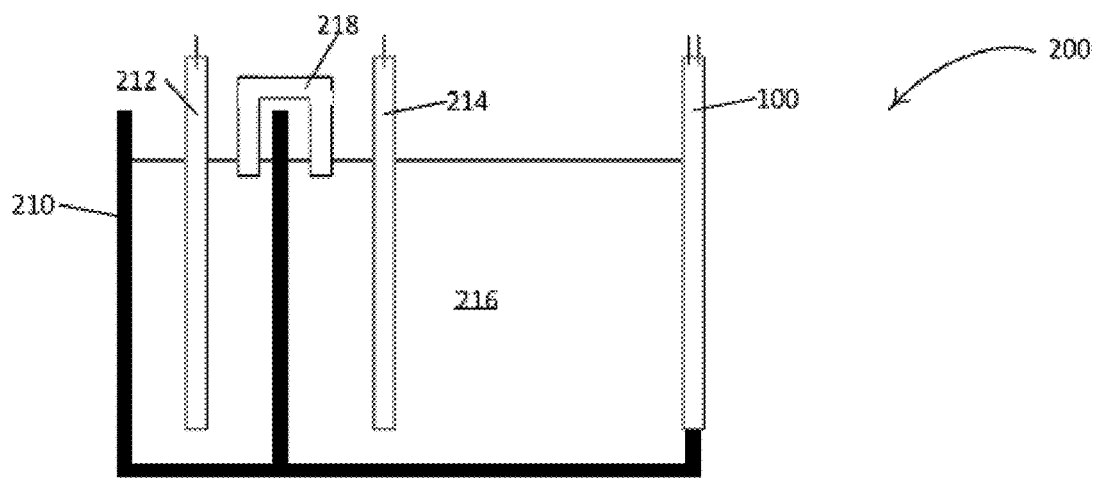
FIG. 2

SYSTEMS, DEVICES, AND METHODS FOR ELECTROCHEMICAL WATER ANALYSIS

RELATED APPLICATION

This application claims the benefit of the filing date of Application No. 63/315,192, filed on 1 Mar. 2022, the contents of which are incorporated herein by reference in their entirety.

FIELD

The disclosure is generally directed at water analysis and, more specifically, at electrochemical analysis of water using a quartz crystal microbalance.

BACKGROUND

Manganese (Mn) is an emerging contaminant in drinking water. It was previously only considered to be an aesthetic issue, until recent epidemiologic evidence has suggested a negative impact on the neurological development on children. To address the health impact of Mn, a new health-based maximum acceptable concentration was developed by Health Canada (2019) and proposed by World Health Organization (2020). Current analytical methods recommended by US EPA and "Standard Methods for the Examination of Water and Wastewater" (2017) are accurate for analyzing drinking water, but are not appropriate for field testing as they require bench-sized spectroscopic equipment. The water industries are looking for a more compact and less expensive method to achieve analysis on site.

Electrochemical techniques are based on measurement of an analyte upon the application of an electric input. Cathodic stripping voltammetry (CSV) is a popular conventional electrochemical technique for Mn analysis, and it promises sensitive measurement of Mn at nM levels, but no device based on CSV is commercially available for Mn analysis, possibly due to matrix interference. Berg et al. (2016) achieved a limit of detection (LOD) of 500 nM using stencil-printed carbon ink electrode and CSV; however, the method was found to be susceptible to aluminum(III), copper(II), iron(II), and lead(II) at concentration ratios at or below one. Kang et al. (2017) used a platinum thin film electrode with CSV and also showed that Pb(II) and Fe(II) interfere with Mn analysis.

The most common source of interference comes from redox reactions involving interfering reagents, where interfering reagents may either be oxidized or reduced by conventional electrochemical methods, but typically not both. Many interfering reagents may therefore interfere with the results of conventional electrochemical measurement of Mn when the electrochemical techniques require both the oxidation and reduction reaction of Mn for the analysis, such as cyclic voltammetry, CSV and anodic stripping voltammetry.

SUMMARY

In one aspect of the disclosure, there is provided a system and method for electrochemical analysis of water.

In another aspect, there is provided a method for quantifying an analyte in water, comprising: exposing a piezoelectric material having at least one electrode disposed thereon to the water; electrodepositing the analyte on the electrode by applying an electrical potential to the electrode while simultaneously measuring an electrical current through the electrode as a function of time and a frequency shift of vibration of the piezoelectric material as a function of time; using the measured electrical current as a function of time to determine a charge on the electrode and the measured frequency shift as a function of time to determine a mass of the analyte deposited on the electrode; and using the charge on the electrode and the mass of the analyte deposited on the electrode to determine a concentration of the analyte in the water.

In one embodiment, the electrical potential applied to the electrode is a stepped voltage.

In one embodiment, the electrical potential applied to the electrode is an alternating voltage.

In one embodiment, the frequency shift of the piezoelectric material is measured as a frequency of a voltage of the piezoelectric material.

In one embodiment, the method comprises preparing a calibration curve for the analyte, and using the calibration curve to determine the concentration of the analyte in the water.

In one embodiment, the method comprises cleaning the electrode on the piezoelectric material with an acid prior to electrodepositing the analyte.

In one embodiment, the method comprises using a processor to execute an algorithm that directs the processor to receive measurement data corresponding to the measured electrical current through the electrode as a function of time and the frequency shift of vibration of the piezoelectric material as a function of time; calculate the charge on the electrode and the measured frequency shift as a function of time; calculate the mass of the analyte deposited on the electrode; use the charge on the electrode and the mass of the analyte deposited on the electrode to calculate the concentration of the analyte in the water; and output a value of the concentration of the analyte in the water.

In another aspect, there is provided an apparatus for quantifying an analyte in water, comprising: a cell that is adapted to contain the water; a piezoelectric material removably disposed in the cell, the piezoelectric material having at least one electrode disposed thereon, wherein the at least one electrode is exposed to the water when the water is contained in the cell; a measuring device that controls electrodepositing the analyte on the electrode by applying an electrical potential to the electrode while simultaneously measuring an electrical current through the electrode as a function of time and a frequency shift of vibration of the piezoelectric material as a function of time; a data processing device including a processor that executes an algorithm stored on non-volatile memory, wherein the algorithm directs the processor to: receive measurement data from the measuring device corresponding to the measured electrical current through the electrode as a function of time and the frequency shift of vibration of the piezoelectric material as a function of time; calculate the charge on the electrode and the measured frequency shift as a function of time; calculate the mass of the analyte deposited on the electrode; use the charge on the electrode and the mass of the analyte deposited on the electrode to calculate the concentration of the analyte in the water; and output a value of the concentration of the analyte in the water; the apparatus further comprising a controller that controls operation of the measuring device and the processing device.

In one embodiment, the apparatus comprises a communications device that enables the apparatus to communicate with at least one other device over a network; wherein the communications include transmitting the value of the concentration of the analyte in the water to the at least one other device.

In one embodiment, the electrical potential applied to the electrode is a stepped voltage.

In one embodiment, the electrical potential applied to the electrode is an alternating voltage.

In one embodiment, the frequency shift of the piezoelectric material is measured as a frequency of a voltage of the piezoelectric material.

In one embodiment, the apparatus calculates the concentration of the analyte in the water; and outputs a value of the concentration of the analyte in the water at least partially automatically.

In one embodiment, the apparatus is configured to obtain a water sample for analysis from a water distribution system.

According to certain aspects and embodiments described herein, the piezoelectric material may comprise a quartz crystal.

According to certain aspects and embodiments described herein, the water may be a drinking water sample.

According to certain aspects and embodiments described herein, the analyte may be manganese.

BRIEF DESCRIPTION OF THE DRAWINGS

Embodiments of the invention will now be described, by way of example only, with reference to the accompanying drawings, wherein:

FIG. 1A is a front view of a quartz crystal microbalance (QCM) crystal according to an embodiment.

FIG. 1B is a top view of the QCM crystal of FIG. 1A.

FIG. 2 is a schematic diagram of an electrochemical QCM (EQCM) cell 200 according to an embodiment.

DETAILED DESCRIPTION OF EMBODIMENTS

Figure 3:
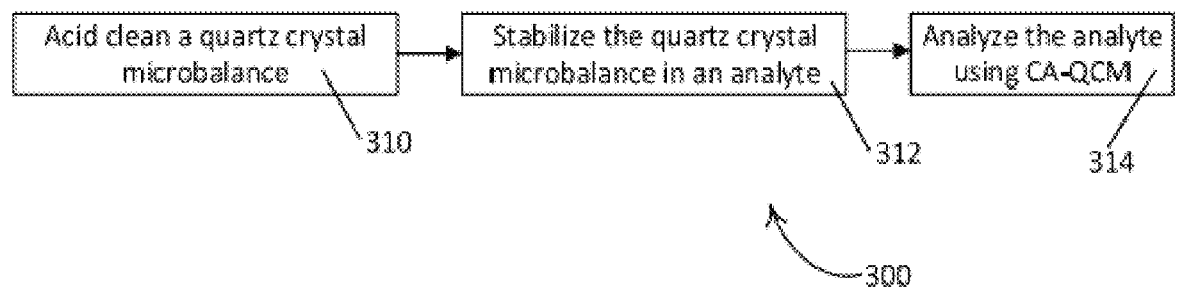
FIG. 3 is a flow diagram for a method of analyzing water using chronoamperometry (CA) and QCM, according to an embodiment.

The disclosure is generally directed at a system for the electrochemical analysis of water. In one embodiment, the disclosure is directed at devices, i.e., apparatus, for use in a system for electrochemical analysis of water. In another embodiment, the disclosure is directed at a method for electrochemical analysis of water. The systems, devices, and methods of the disclosure include chronoamperometry (CA) combined with a piezoelectric mass balance based on a crystal resonator such as quartz, topaz, tourmaline, etc. For the purpose of this disclosure, the example of a quartz crystal microbalance (QCM) will be used. Without being bound to any particular theory, the disclosure asserts that the combination of CA and QCM (CA-QCM) reduces the effect of interfering reagents on the determination of the concentration of an analyte of interest relative to conventional electrochemical techniques. In select embodiments, CA-QCM reduces the effect of interfering reagents on the determination of the concentration of $Mn^{2+}$ in water. A person of ordinary skill in the art, having the benefit of this disclosure, will appreciate that CA-QCM may be used to determine the concentration of analytes in water other than $Mn^{2+}$, however, the disclosure will refer to $Mn^{2+}$ in the following description for the sake of clarity.

Since CA-QCM oxidizes $Mn^{2+}$ but does not require reduction of Mn, CA-QCM is less likely to be affected by interfering reagents that are already in their highest oxidation state in water. The most abundant forms of many metal ions in drinking water are already at their highest oxidation state (e.g., $Fe^{3+}$, $Cu^{2+}$), which make CA-QCM less susceptible to interference. CA-QCM may thereby show increased resistance to interfering agents compared to conventional electrochemical techniques for detecting $Mn^{2+}$ in water. The most abundant form of Mn in drinking water is soluble $Mn^{2+}$ and insoluble $MnO_2$. Soluble $Mn^{2+}$ in water can be oxidized to $MnO_2$ by electrochemistry and deposited on the electrode surface. CA-QCM may be performed in an electrochemical quartz crystal microbalance (EQCM) cell.

FIG. 1A is a front view of a QCM crystal device 100 according to an embodiment. FIG. 1B is a top view of the QCM crystal device 100. The QCM crystal device 100 includes a quartz crystal 110, two electrodes 112a, 112b positioned on opposite sides of the quartz crystal 110, and two electrical contacts 114. Each electrical contact 114 is coupled to a respective electrode 112a, 112b. Each electrode 112a, 112b may include gold (Au), however in select embodiments the electrode may be or include platinum or other materials. Each electrode 112a, 112b may be coupled to the quartz crystal 110 via an adhesive layer. In some embodiments the quartz crystal may have only one electrode. For example, a quartz crystal having an electrode only on one side may be used.

FIG. 2 is a schematic diagram of an EQCM cell 200 according to an embodiment. The EQCM cell 200 includes a QCM crystal device 100, a container 210, a counter electrode 212, and a reference electrode 214. In select embodiments, the EQCM cell may not include the reference electrode 214. However, using the reference electrode allows the electric potential for electrochemical measurement to be applied more accurately. In use, the container 210 contains a solution 216 which may be a water sample containing an analyte of interest, for example Mn'. The QCM crystal device 100 is positioned in the container to enable one electrode 112a (i.e., the working electrode) to be in contact with the solution 216, while the other electrode 112b is not in contact with the solution 216. In some embodiments, both the electrodes 112a and 112b may be used for measurements. In select embodiments, the reference electrode 214 is electrically coupled to the QCM crystal device 100 and the counter electrode 212 via a salt bridge 218. The QCM crystal device 100, the counter electrode 212, and the reference electrode 214 may be electronically coupled to electronic instruments to perform CA and QCM measurements. The EQCM cell 200 may include a Faraday cage to reduce electromagnetic interference during CA and QCM measurements.

CA is an electrochemical technique in which a stepped potential is applied to an electrode, while the current change is monitored as a function of time (i.e., i-t curve). CA is able to electrodeposit an analyte (for example, $MnO_2$) on one electrode 112a or 112b by applying a constant potential to the electrode 112a or 112b. In the case of $MnO_2$, where Mn' is the analyte, a positive deposition potential is applied. For other analytes such as copper ($Cu^{2+}$) and lead ($Pb^{2+}$), a negative deposition potential is applied. QCM measures the frequency shift ($\Delta f$) of a quartz crystal within a QCM to measure the mass change ($\Delta m$) on the microbalance as a function of time (i.e., f-t curve). The vibration of the quartz crystal follows a piezo effect. A positive change of mass results in a negative change of frequency. QCM uses the piezo effect of the quartz crystal 110 when an alternating current is applied across the two electrodes 112a, 112b to measure the frequency of the QCM crystal device 100. Any change in mass ($\Delta m$) resulting from the deposition of material due to CA is measured by measuring the frequency of the QCM crystal device 100 for a frequency shift $\Delta f$. CA-QCM integrates the two techniques to measure the current applied during CA and the $\Delta f$ simultaneously. No research or literature has been identified that uses this technique to measure Mn solution concentration, including Mn concentration in drinking water. By integrating CA and QCM, the deposition and removal of the material can be plotted by an i-t curve and an f-t curve.

FIG. 3 is a flow diagram for a method 300 of analyzing water using CA and QCM, according to an embodiment. The method 300 may be performed using a EQCM cell 200, such as, for example, the embodiment shown in FIG. 2. At 310, a QCM crystal is acid cleaned. Acid cleaning the QCM crystal may include contacting the QCM crystal with an acidic solution and applying a voltage to the QCM crystal to remove material from the QCM crystal. Acid cleaning the QCM crystal may also include contacting a counter electrode with the acidic solution, and/or may include contacting a reference electrode with the acidic solution. The acidic solution may be a weakly acidic solution, i.e., a weakly diluted acid but strong enough to clean the electrode surface (e.g., 0.1 M to 0.5 M). For example, the acidic solution may be diluted sulfuric acid ($H_2SO_4$), diluted nitric acid ($HNO_3$), diluted hydrochloric acid (HCl), or diluted phosphoric acid ($H_3PO_4$). Acid cleaning may include acid cleaning the QCM crystal in an EQCM cell 200.

At 312, the QCM crystal is stabilized in an analyte. Stabilizing the QCM crystal in an analyte includes contacting the QCM crystal with an analyte solution for a period of time prior to analyzing the analyte. The analyte may be a water sample containing $Mn^{2+}$. In one specific embodiment, stabilizing the QCM crystal may be performed for a period of 300 s or longer.

At 314, the analyte is analyzed using CA-QCM. Analyzing the analyte includes applying a voltage to the QCM crystal. The voltage may be a chronoamperometry voltage applied as a step voltage. The chronoamperometry voltage may be applied between a counter electrode and one QCM crystal electrode. The voltage may be a QCM voltage applied as an alternating voltage. The QCM voltage may be applied across two QCM crystal electrodes. Analyzing the analyte includes recording signals. Non-exclusive examples of signals include a change in frequency of the QCM crystal and a total charge transferred. The change in frequency may be recorded as a change in the frequency of the QCM voltage. The total charge transferred may be a total charge transferred between the counter electrode and the one QCM crystal electrode. Analyzing the analyte includes comparing recorded signals to a calibration curve to determine an analyte concentration of the analyte.

Figure 4:
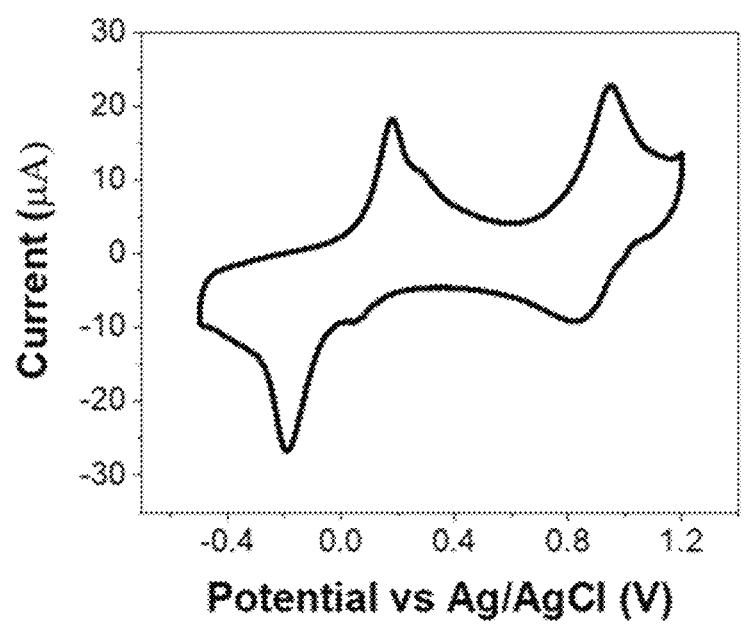
FIG. 4 illustrates a cyclic voltammogram of an aqueous $Mn^{2+}$ solution, according to an embodiment.

FIG. 4 illustrates a cyclic voltammogram of an aqueous $Mn^{2+}$ solution, according to an embodiment. Two major oxidation peaks are observed at approximately 0.2 V and 1.0 V, respectively. The 0.2 V oxidation peak corresponds to the oxidation from soluble Mn(II) to soluble Mn(III), while the 1.0 V oxidation peak corresponding to the oxidation from soluble Mn(III) to insoluble Mn(IV). The oxidation potential of CA was optimized by depositing Mn at different potentials.

Figure 5:
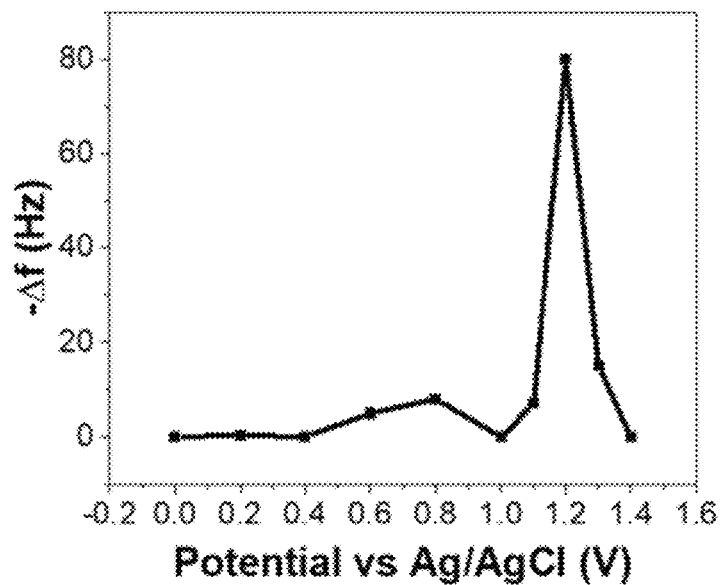
FIG. 5 illustrates the variability of frequency shift ($\Delta f$) after Mn deposition performed by altering the deposition voltage, according to an embodiment.

FIG. 5 illustrates the variability of frequency shift ($\Delta f$) after Mn deposition performed by altering the deposition voltage, according to a specific embodiment. To determine the relationship between deposition potential and deposition amount, and thereby improve Mn detection, the $\Delta f$ was measured in 50 μM $Mn^{2+}$ solution under different deposition potentials for 5 min each. The $\Delta f$ is plotted at each corresponding deposition potential in FIG. 5. The deposition potential of 1.2 V was identified as a value of interest to determine Mn concentration, as $\Delta f$ reached a maximum or high level at 1.2 V. The formation of $MnO_2$ occurs when the applied potential is 1.2 V, however when the potential is higher than 1.2 V, the amount of $MnO_2$ that is deposited on the electrode dropped, which may be due to the nucleation process of $MnO_2$. At higher potentials, the $MnO_2$ film was observed to be less homogeneous and potentially unstable.

Figure 6:
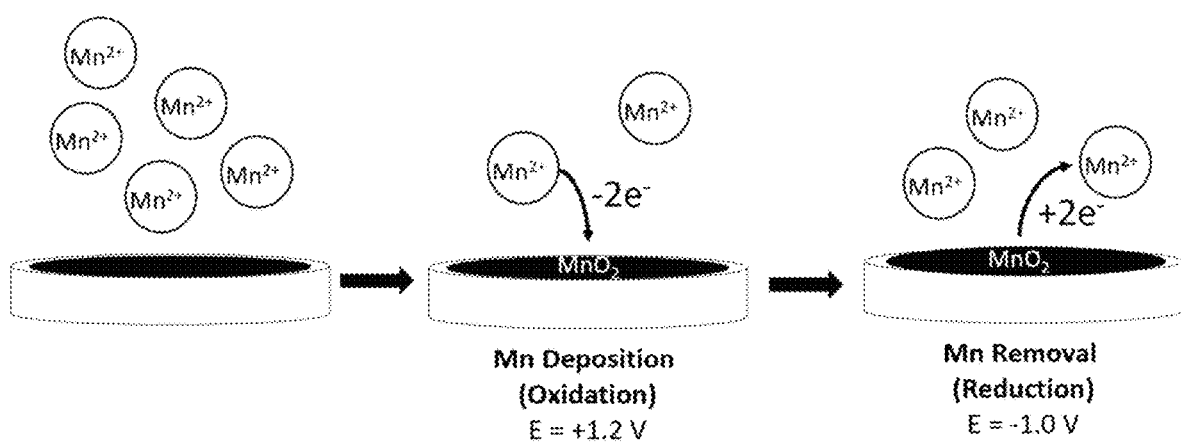
FIG. 6 is a schematic diagram of Mn deposition and removal, according to an embodiment.

FIG. 6 is a schematic diagram of Mn deposition and removal, according to an embodiment. CA-QCM uses a redox reaction to deposit or remove Mn from water. As shown in FIG. 6, when a +1.2 V potential is applied, soluble Mn2+ is oxidized to insoluble $MnO_2$ and deposited on the electrode surface. The mass of the crystal increases as $MnO_2$ is deposited on the electrode, which causes a decrease of frequency. The total charge transfer (Q) measured by CA during deposition also indicates how much deposition occurs on the electrode, since redox reactions involve electron transfer between two species and result in a current. As described below, the deposition rate of $MnO_2$ is positively correlated with the concentration of $Mn^{2+}$. In other words, a higher concentration of Mn results in a greater $\Delta m$ due to $Mn^{2+}$ deposition.

Figure 7A:
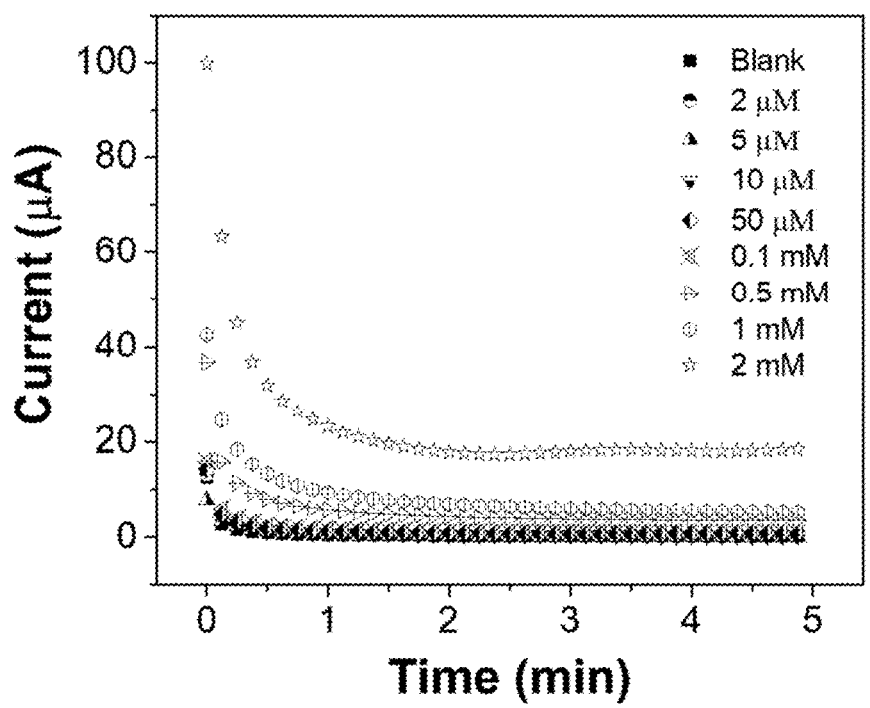
FIG. 7A illustrates the variability of CA measurements by altering the $Mn^{2+}$ concentration, according to an embodiment.
Figure 7B:
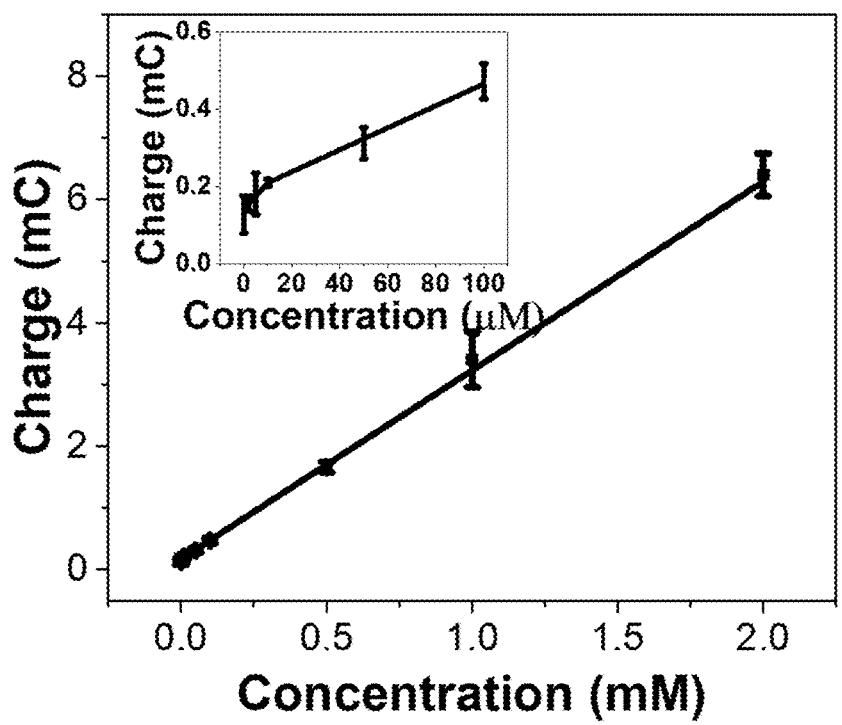
FIG. 7B illustrates a calibration curve obtained using the results illustrated in FIG. 7A.
Figure 7C:
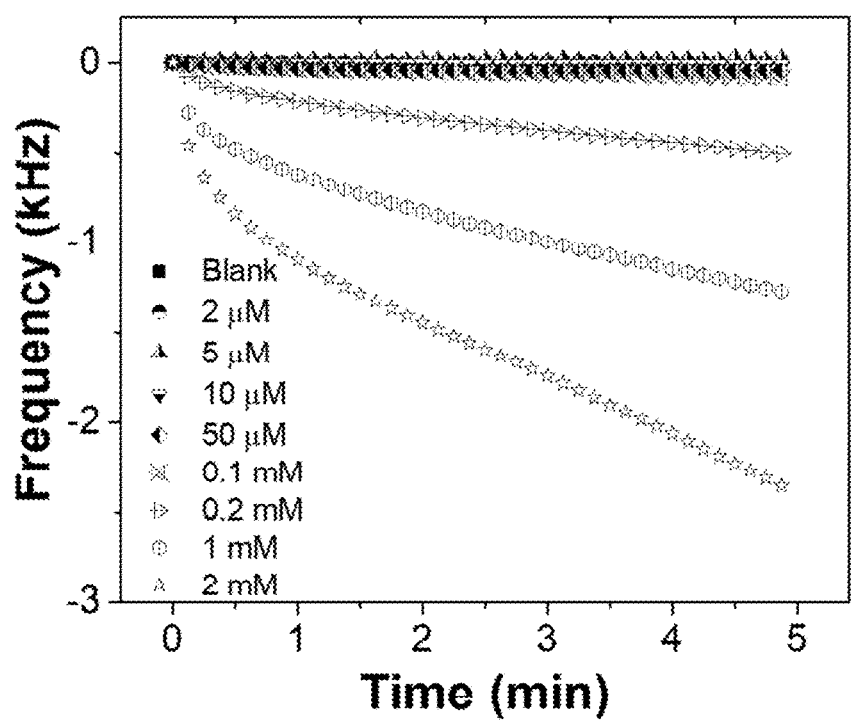
FIG. 7C illustrates the variability of $\Delta f$ measurements by altering the $Mn^{2+}$ concentration, according to an embodiment.
Figure 7D:
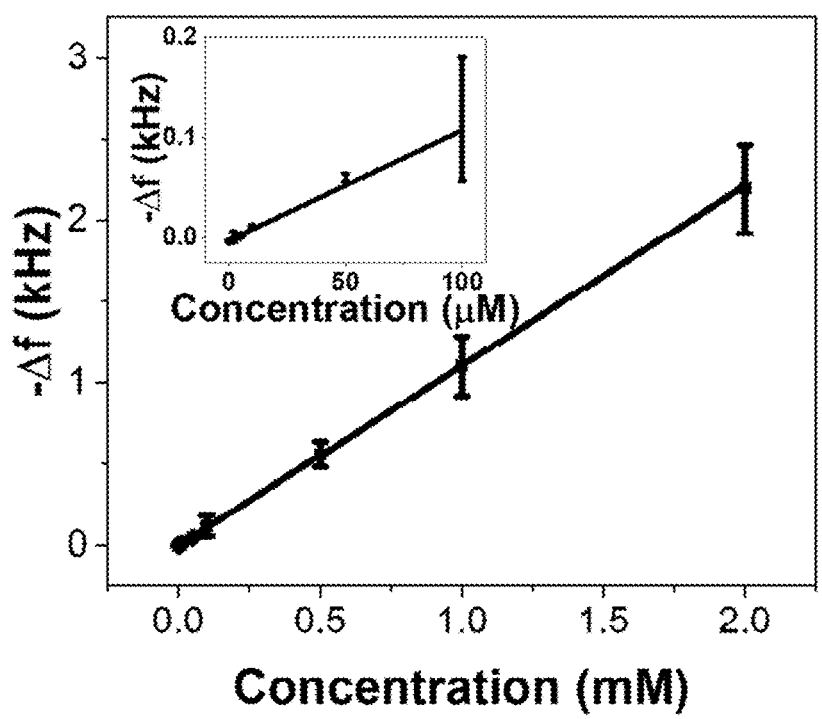
FIG. 7D illustrates a calibration curve obtained using the results illustrated in FIG. 7C.

In an embodiment, the concentration of $Mn^{2+}$ may be determined from CA-QCM measurements via a calibration curve obtained using solutions having different Mn concentrations without the presence of any interfering agents. FIG. 7A illustrates the variability of chronoamperometry (CA) measurements by altering the $Mn^{2+}$ concentration. FIG. 7B illustrates a calibration curve obtained using the results illustrated in FIG. 7A. FIG. 7C illustrates the variability of $\Delta f$ measurements by altering the $Mn^{2+}$ concentration. FIG. 7D illustrates a calibration curve obtained using the results illustrated in FIG. 7C. In one embodiment the Mn concentrations may be varied from 0 to 2 mM. As shown in FIG. 7A, a spike in current after the application of the +1.2 V potential is observed due to initial electrolysis of the analyte at the electrode surface, followed by the current decay over time until reaching a plateau (due to the diffusion of the analyte). Higher current values are observed for Mn at higher concentrations. The total charge may be calculated by the integration of current over time. As shown in FIG. 7B, the total charge of various concentrations shows two steps of linear calibration curve between 0 to 2 mM. The error bars are defined as the standard deviation of measurements by three different quartz crystals. Charge values of lower Mn concentrations from 0 to 100 µM are plotted in the small window of FIG. 7B. The equation of linear regression from 0 to 10 µM Mn is y=6.98Conc.(M)+0.000140 ($r^2$=0.98). The equation of linear regression from 10 µM to 2 mM is y=3.06Conc.(M)+0.000172 ($r^2$=0.99). The f-t curve obtained simultaneously with the i-t curve using CA-QCM analysis is shown in FIG. 7C. For each Mn concentration, the frequency change rate decreases over time until stable, due to the diffusion of the analyte in the sample solution. Comparing among different Mn concentrations, the frequency change is more rapid for higher Mn concentration samples, as more $MnO_2$ is deposited on the crystal per unit of time. The total $\Delta f$ of QCM may be plotted for each concentration as shown in FIG. 7D. A linear calibration curve was obtained for $-\Delta f$ vs. Mn concentration. The equation of the linear regression is y=1.11Conc.(µM) −43.18 ($r^2$=0.97). $-\Delta f$ of lower Mn concentrations from 2 to 100 µM is plotted as shown in the small window of FIG. 7D. The sensitivity of the technique may be determined by calculating their respective limits of detection (LOD).

The LOD of both CA and QCM were determined for this embodiment by seven replicated measurements in a blank (Milli-Q water) solution. The standard deviation (SD) of the total charges is 19 µC and the SD of the total $\Delta f$ is 4.9 Hz. The LOD is then calculated by $$LOD=3\sigma/m$$

where m is the slope of the calibration curve, and $\sigma$ is the standard deviation of the blank, which is very close to the SD of the seven replicated measurements. The LOD calculated for CA is 8.2 µM, while the LOD for QCM is 13.2 µM. The maximum acceptable concentration (MAC) from Canadian Drinking Water guideline is 2.18 µM. Even though the LOD of CA and QCM are both slightly higher than the MAC, CA is more sensitive than QCM and the LOD is closer to the MAC value. The total $\Delta m$ determined by CA or QCM can be calculated by its total charge transfers or the frequency change.

When an electrode reaction takes place, both faradaic and non-faradaic processes can occur simultaneously. During a faradaic process, the amount of redox reaction occurring on the electrode is directly proportional to the amount of charge; however, when charge transfer reactions are thermodynamically or kinetically unfavorable in a specific range of potentials or under low concentration of analyte, non-faradaic processes occur. In this embodiment, each Mn concentration was analyzed by three different quartz crystals. Each electrode charge was calculated from the integration of current over time, and the total $\Delta f$ of the quartz crystal was obtained from the last frequency value of the QCM data. The mass change of $MnO_2$ determined by CA ($\Delta m_{CA}$) is proportional to the amount of charge. The $\Delta m_{CA}$ assumes that all the charges are assumed to be transferred across the Au electrode-solution interface, which means all the electron transfer causes the oxidation reaction of $Mn^{2+}$. The charge of one electron is $1.6\times10^{-19}$ C, and each $Mn^{2+}$ requires 2 electrons to be oxidized to $MnO_2$; therefore, the number of $MnO_2$ deposited on Au is:

$$n=Q \div 2 \div (1.6\times10^{19}) \text{ mol} \quad (1)$$

The molar mass of $MnO_2$ is 86.9368, and Avogadro's number is $6.02\times10^{23}$. The $\Delta m_{CA}$ of $MnO_2$ is:

$$\Delta m_{CA}=n\times86.9368 \div (6.02\times10^{23}) \quad (2)$$

The calculation of mass change determined by QCM ($\Delta m_{QCM}$) is given by the Sauerbrey equation (Owen et al. 2007):

$$\Delta f=-2f_0^2/[A(\mu\rho)^{1/2}]\Delta m_{QCM} \quad (3)$$

where $f_0$ is the resonant frequency of the fundamental mode of the crystal (8 MHz for the crystal used in this embodiment), A is the area of the gold disk coated onto the crystal (0.205 $cm^2$), $\rho$ is the density of the crystal (2.648 $g/cm^3$), and $\mu$ is the shear modulus of quartz ($2.947\times10^{11}$ g/cm $s^2$). Therefore, a 1.0 Hz change in frequency corresponds a $\Delta m_{QCM}$ of 1.4 ng. The mass of the deposited $MnO_2$ is:

$$\Delta m_{QCM}=\Delta f\times1.4\times10^{-9} \text{ g} \quad (4)$$

The ratio between $\Delta m_{CA}$ and $\Delta m_{QCM}$ was found to gradually approach 1 with the increase of Mn concentration, which indicates faradaic process and non-faradaic processes co-occurred at lower concentration; while at higher concentration, the majority is faradaic processes.

Figure 8A:
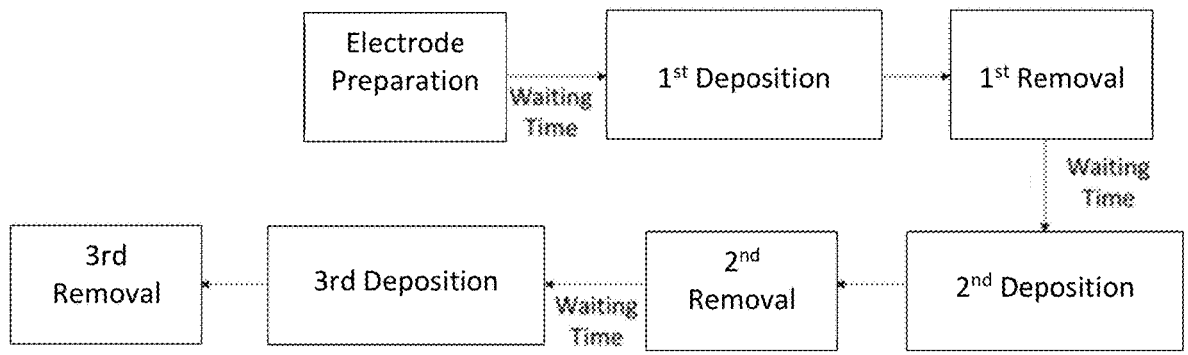
FIGS. 8A and 8B are flow diagrams for methods of cleaning an electrode, according to embodiments.

FIG. 8A is a flow chart for a method of cleaning an electrode, according to an embodiment. The method includes preparing the electrode, performing a first electrode deposition reaction, performing a first removal reaction, performing a second deposition reaction, performing a second removal reaction, performing a third electrode deposition reaction, and performing a third removal reaction. The reproducibility of two different cleaning strategies were compared. The reproducibility was compared by running three replicated CA-QCM tests in 1.0 mM $Mn^{2+}$ solution, with cleaning in acid solution for the first cleaning strategy or cleaning in sample solution for the second cleaning strategy between each measurement. The two cleaning strategies using different solutions were carried out by −1.0 V CA for 300 s. When cleaning in sample solution, the cleaning procedure was carried out in the Mn sample without changing into another solution. The acid solution cleaning strategy used 0.1 M $H_2SO_4$ as electrolyte solution for the cleaning. An embodiment is shown in FIG. 8B.

Figure 8B:
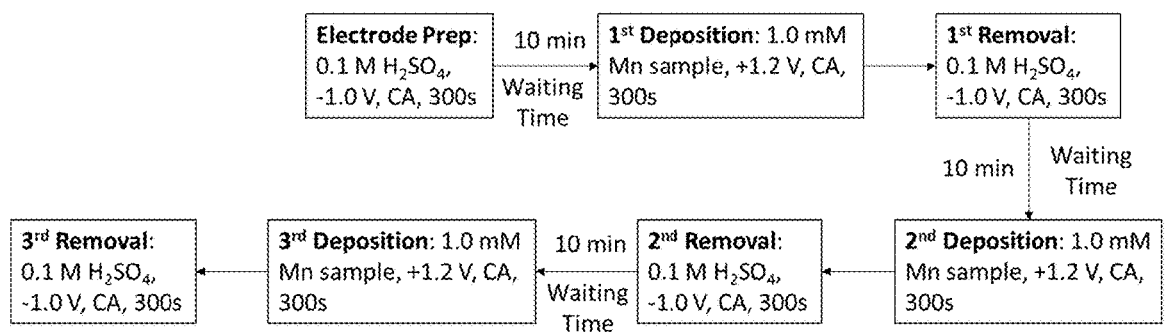
Figure 9A:
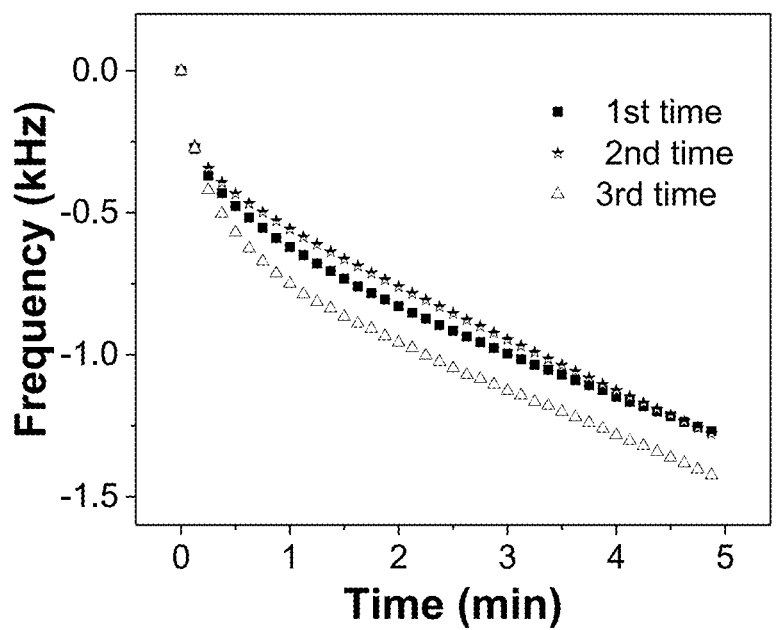
FIGS. 9A-9D illustrate the variability of $\Delta f$ measurements during the electrode cleaning method of FIG. 8B.
Figure 9B:
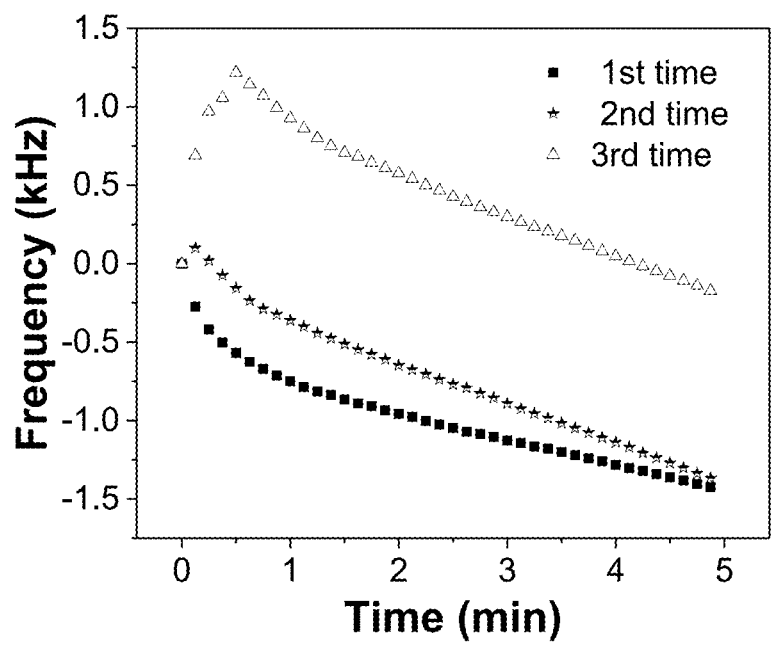
Figure 9C:
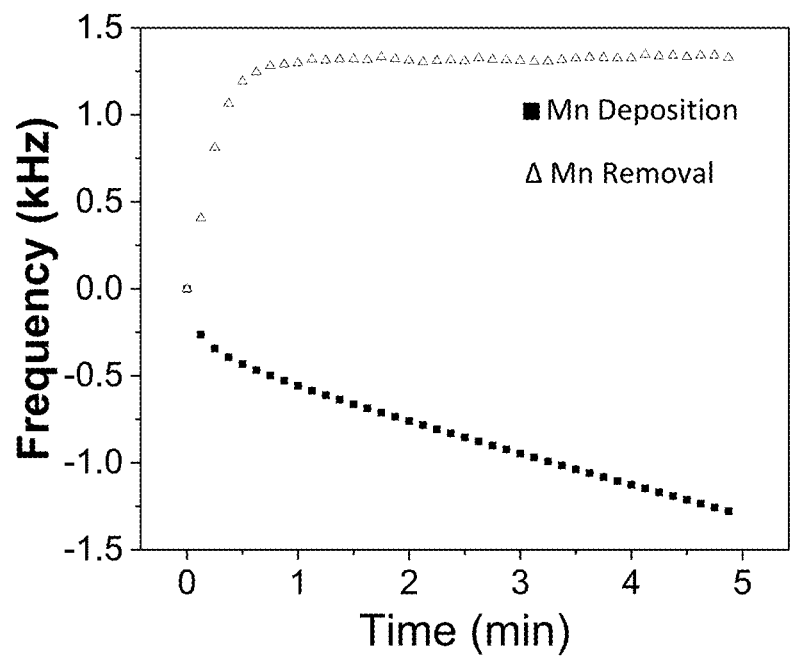
Figure 9D:
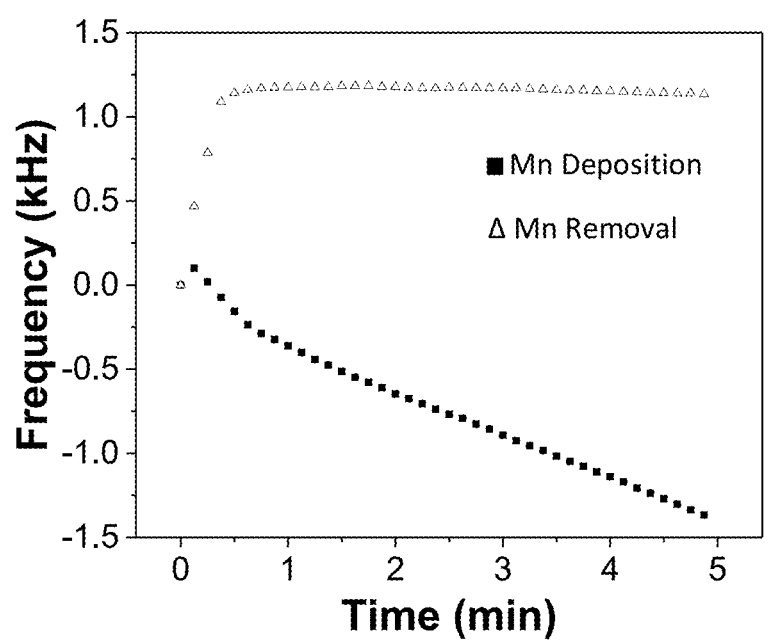

FIGS. 9A-9D illustrate the variability of $\Delta f$ measurements during the electrode cleaning method of FIG. 8B. FIGS. 9A and 9B show f-t curves obtained from A) three replicated measurements in 1.0 mM Mn solution using acid cleaning method, and B) three replicated measurements in 1.0 mM Mn solution using sample cleaning method. FIGS. 9C and 9D show the second of the three Mn deposition and removal f-t curves using the acid cleaning method and the sample cleaning method, respectively. As shown in FIGS. 9A and 9B, the Mn f-t results after cleaning in acid solution overlay better than the Mn f-t results after cleaning in sample solution. The Mn deposition and removal in acid or sample solution, shown in FIGS. 9C and 9D, respectively, were used to calculate the mass changes for each procedure. After cleaning in acid solution, the mass change of deposition procedure was 1.82 µg ($\Delta f$=−1302 Hz), and the mass change of the removal procedure was 1.87 µg ($\Delta f$=−1338 Hz), which indicates the $MnO_2$ was completely removed from the electrode. However, the mass change of deposition and removal by cleaning in sample solution were 1.96 µg ($\Delta f$=−1403 Hz) and 1.58 µg ($\Delta f$=−1130 Hz), respectively. This indicates that after cleaning in sample solution, the Mn material was not completely removed from the electrode, as the mass change of removal procedure was smaller than deposition. In one embodiment, cleaning using a low concentration (0.1 M) $H_2SO_4$ was surprisingly found to be more effective than cleaning in Mn sample solution. Such a weakly diluted acid was found to be sufficient to clean for the reuse of the electrode.

Due to the fact that drinking water is a complex matrix system, several interference studies were carried out to explore the application of the techniques according to embodiments described herein to drinking water with other common interfering reagents. FIGS. 10A-10F illustrate the variability of CA and QCM measurements by the addition of various potentially interfering reagents, according to embodiments.

$KNO_3$

Figure 10A:
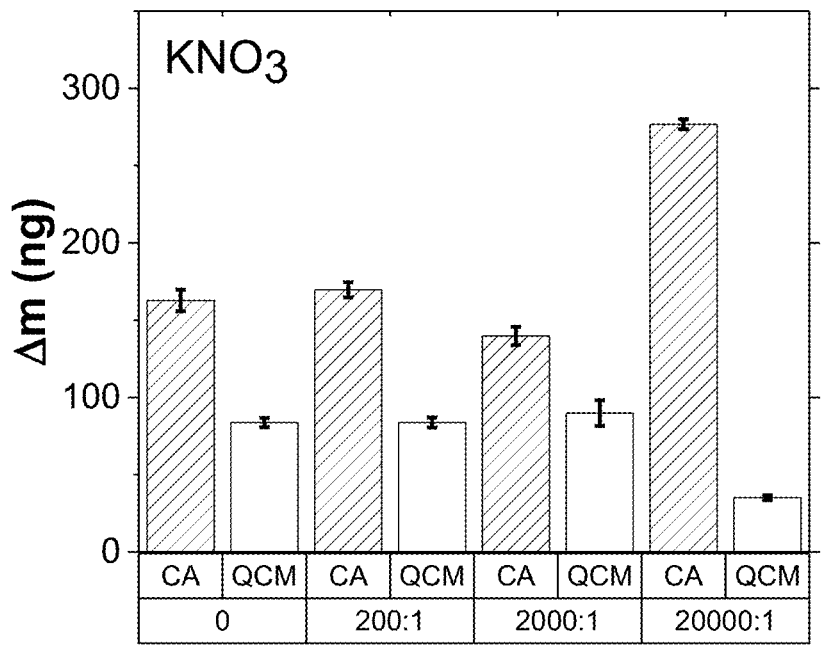
FIGS. 10A-10F illustrate the variability of CA and QCM measurements by the addition of various potentially interfering reagents, according to an embodiment.

The interference of $KNO_3$ is shown in FIG. 10A. Three high amounts of $KNO_3$ were added to 50 µM Mn solution to study their impact on the Mn analysis results. The highest concentration of $KNO_3$ of 1 M is still fully soluble in water. The $K^+$ and $NO_3^-$ ions are both electrochemically stable, which means they do not participant in redox reactions. The amount of $KNO_3$ not only change the concentration of $K^+$ and $NO_3^-$, but also changed the ionic strength of the solution. As shown in FIG. 10A, having 0.01 (200:1) and 0.1 M (2000:1) of $KNO_3$ did not make a significant difference on $\Delta m_{QCM}$; however, at 1 M (20000:1) $KNO_3$, the $\Delta m_{CA}$ increased significantly. The increased amount of charge might be due to the reason that some $K^+$ insert into the cation vacancies during the $MnO_2$ growth. The QCM results decreased at the same time, possibility because high level of $NO_3^-$ ions accumulated on the positive charged electrode surface, which prohibit the reaction of $Mn^{2+}$. Ocean water contains approximately 35000 ppm of salt (0.6 M in NaCl), which makes it impossible to have 1 M salt in drinking water.

Figure 10B:
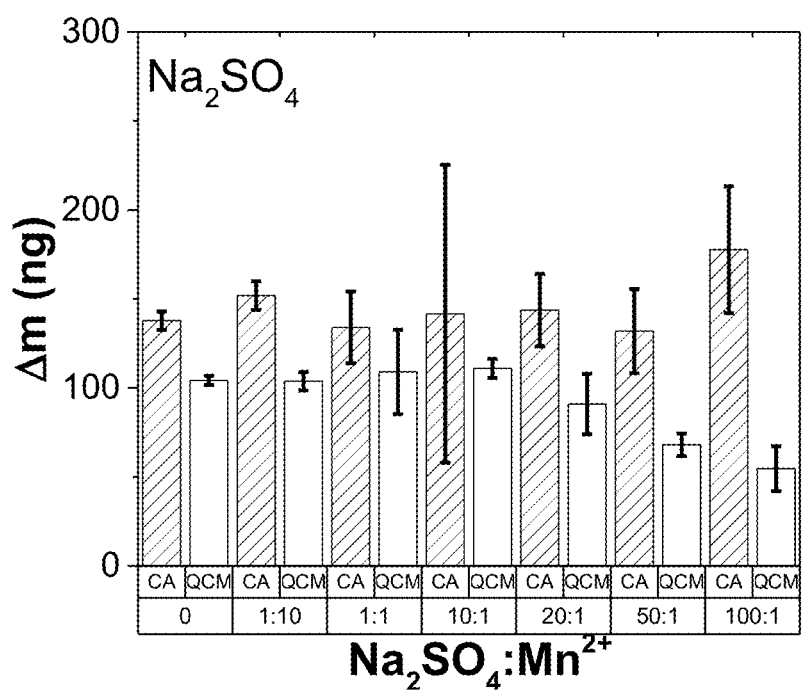

$Na_2SO_4$ $Na_2SO_4$ salt was added to 50 µM $Mn^{2+}$ and the CA and QCM signals were recorded accordingly. The salt fully dissolved in the solution as $Na^+$ and $SO_4^{2-}$ ions. The $Na^+$ and $SO_4^{2-}$ ions are not involved into the redox reaction since they are stable under this electrochemical condition. As shown in FIG. 10B, the mass calculated from QCM gradually decreased when $Na_2SO_4$ was over 20 times the concentration of $Mn^{2+}$, while the mass calculated from CA was more stable and only increased when the $Na_2SO_4$ concentration was over 100 times the Mn' concentration. Both and CA and QCM results show trends similar to the interference study of $KNO_3$ possibly due to the same reason. When having higher concentration of salt, the ionic strength of the solution increases. The frequency change from QCM drops under high ionic strength, while the total charge from CA is the opposite.

$Cu^{2+}$

Figure 10C:
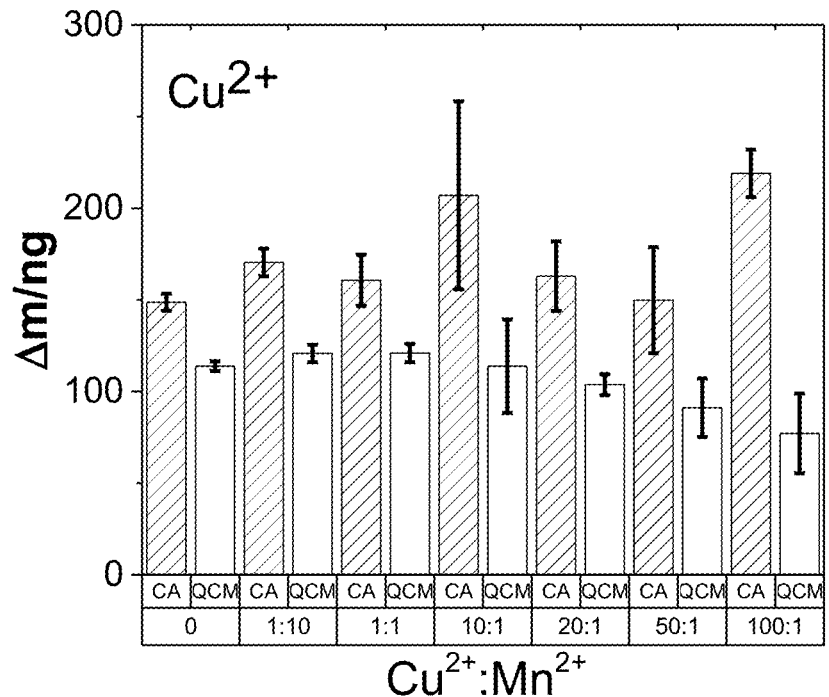

The interference of $Cu^{2+}$ was determined by using the CA-QCM technique on $Mn^{2+}$ solution containing seven different levels of $CuSO_4$. $Cu^{2+}$ is the highest oxidation state of Cu. The $Cu^{2+}$ ions can be reduced to $Cu^+$ or Cu easily; however, it cannot be further oxidized to higher oxidation state. The interference of $Cu^{2+}$ should be small, as no redox reaction would happen at the given electrochemical condition. Only one measurement was carried out for each sample solution, where CA and QCM were determined simultaneously. As shown in FIG. 10C, QCM results show a slightly decreasing trend when the $Cu^{2+}$ concentration is more than 10 times the concentration of Mn'. The mass change calculated by CA seems to be constant at 150 ng, while large random errors are observed for each measurement.

$Fe^{3+}$

Figure 10D:
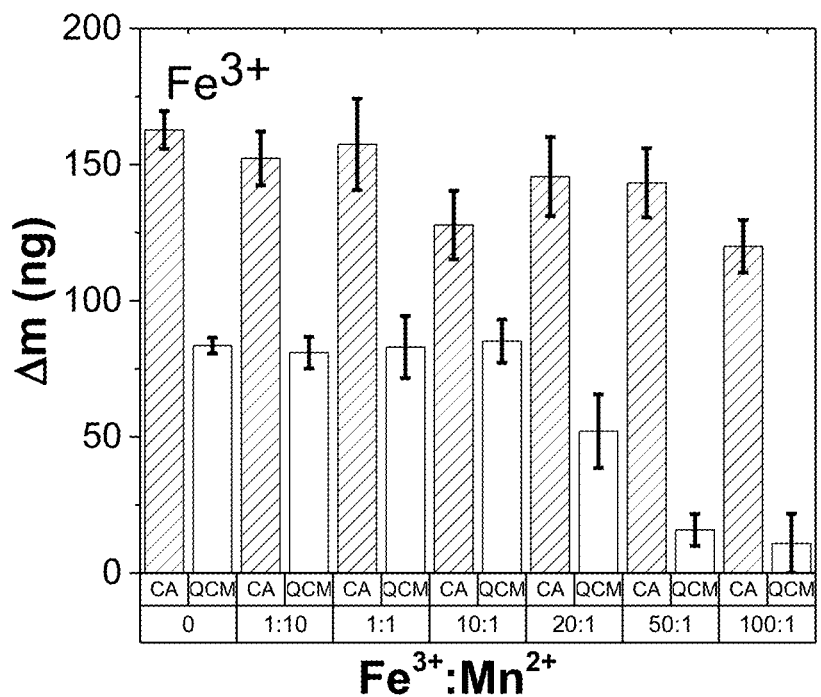

The CA-QCM technique exhibits less interference by most metal ions in drinking water, compared to other measurement techniques, especially for those cannot be further oxidized at the given CA potential. Iron (Fe) ions are commonly found in drinking water, and it is often found co-occur with Mn as they have very similar chemical properties. Fe is one of the common interfering agents of Mn for many other electrochemical techniques. As shown in FIG. 10D, the interference of $Fe^{3+}$ at 0.1, 1, and 10 times Mn concentration is small, due to the fact that $Fe^{2+}$ ions cannot be oxidized to higher oxidation states at +1.2 V. When $Fe^{3+}$ was 20 times higher than Mn concentration, the $\Delta m_{CA}$ stayed the same; however, the $\Delta m_{QCM}$ decreased. The high level of $Fe^{2+}$ compete with $Mn^{2+}$ on the electrode, resulting in a lower oxidizing rate of $Mn^{2+}$. When having high levels of $Fe^{3+}$, CA shows less interference than QCM.

$Fe^{2+}$

Figure 10E:
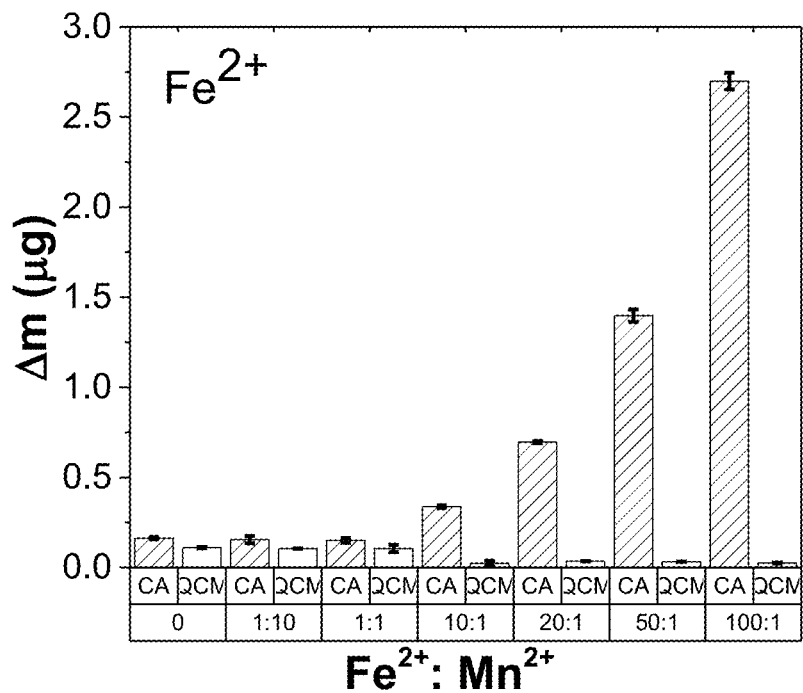

In drinking water, the majority of Fe exists as $Fe^{3+}$. A small amount of $Fe^{2+}$ also exits in drinking water environment and $Fe^{2+}$ can be oxidized to $Fe^{3+}$ by the CA-QCM technique. The oxidation of $Fe^{2+}$ might compete with the oxidation of Mn, which as a result, might cause interference during the Mn analysis. As shown in FIG. 10E, the real mass change first increases slightly over concentration, then decreases when $Fe^{2+}$ is 10 times higher than Mn' concentration. The increase of mass change at lower $Fe^{2+}$ might be due to the co-precipitation of Mn and Fe; however, when the concentration of $Fe^{2+}$ is more than 10 times higher than $Mn^{2+}$, the Mn oxidation is suppressed by the oxidation of $Fe^{2+}$. When $Fe^{2+}$ is 10 and 20 times higher than $Mn^{2+}$, the $\Delta m_{CA}$ increased significantly due to the oxidation reaction of $Fe^{2+}$. $\Delta m_{QCM}$ although decreased slightly when $Fe^{2+}$ is higher than 10 times the concentration of Mn, the QCM results were more stable than CA. $\Delta m_{CA}$ and $\Delta m_{QCM}$ show opposite results at high $Fe^{2+}$ concentrations, which also indicate other reducing agents present in the system. Berg et al. (2016) reported that the CSV method was found to be susceptible to $Fe^{2+}$ at concentration ratios below one. The CA-QCM method is more resilient than CSV. What's more, according to the Toronto Drinking Water Analysis Summary (2020), the average level of Iron was 0.058 mg/L (1.0 µM). The chance of having Fe at mM level is very low.

Humic Acid (HA)

Figure 10F:
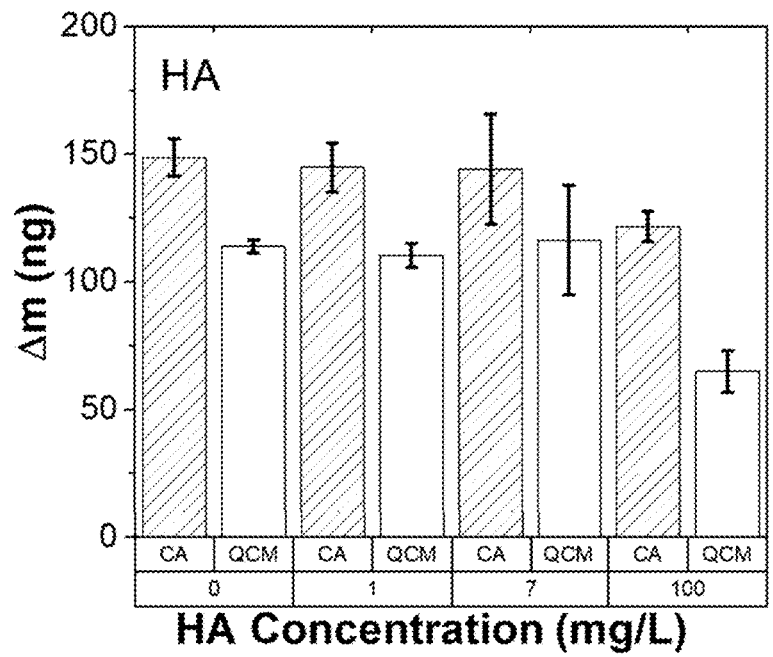

Humic acids are a group of organic molecules and are a significant component of organic matter found in source water. Humic acid of 1, 7, and 100 mg/L levels were used to determine the interference of organic matter. As shown in FIG. 10F, both the CA and QCM signals are stable at 1 and 7 mg/L HA levels, while the signals dropped at 100 mg/L HA level. For drinking water detection, 1 mg/L HA is considered a low concentration, while 7 mg/L HA is a high concentration of organic matter. In this case, the interference effect of HA is small for Mn detection.

Implementation

The technique of CA-QCM combines CA and QCM, which gives more stable results for detecting analytes, including $Mn^{2+}$, than prior techniques. A linear range may be obtained for using both CA and QCM between 0 and 2 mM of Mn' without interfering reagents, with LODs of 8.2 µM and 13.2 µM, respectively for CA and QCM. CA-QCM shows more resilient results to metal ions that are at their highest oxidation states (such as, $Fe^{2+}$, $Cu^{2+}$, $K^+$ and $Na^+$) than ions that can be further oxidized to higher oxidation states (such as $Fe^{2+}$). CA-QCM also provides the possibility for detecting a high $Fe^{2+}$ concentration. When $Fe^{2+}$ is over 10 times higher than $Mn^{2+}$, the $\Delta m_{CA}$ and $\Delta m_{QCM}$ show opposite results for $Mn^{2+}$. The technique is also resistant to high levels of common counter ions in drinking water (e.g., $SO_4^{2-}$, $NO_3^-$) and extremely resistant to high ionic strength.

Figure 11:
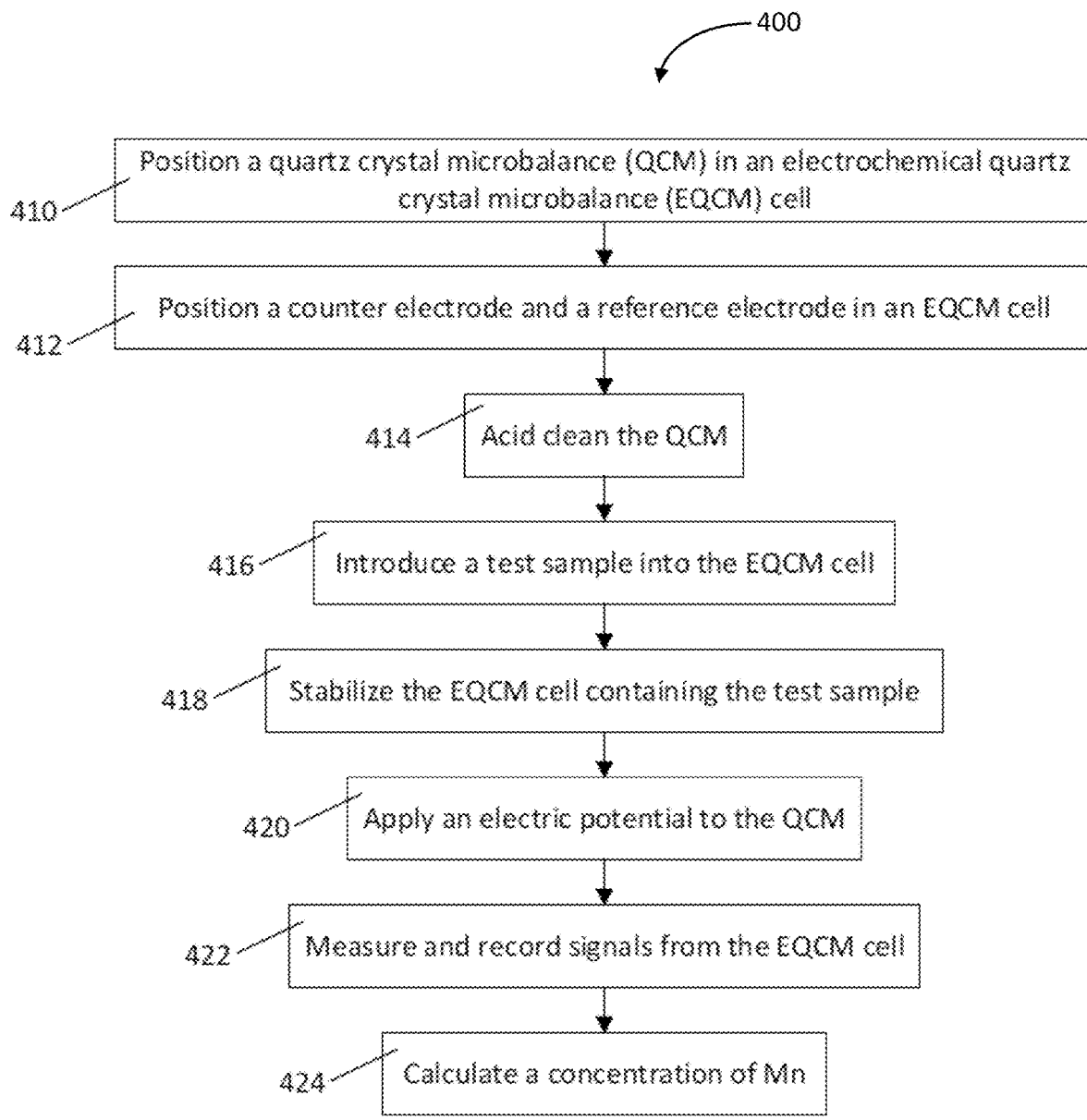
FIG. 11 is a flow diagram for a method of analyzing water using CA and QCM, according to another embodiment.

FIG. 11 is a flow diagram for a method 400 of analyzing water using CA and QCM, according to one embodiment. At 410, a QCM is positioned within an EQCM cell. At 412, a counter electrode and a reference electrode are positioned in an EQCM cell. At 414, the QCM is acid cleaned. The QCM may be acid cleaned while positioned within the EQCM cell. The QCM may also be acid cleaned in the presence of the counter electrode and the reference electrode.

At 416, a test sample is introduced into the EQCM cell. The test sample may partially fill the EQCM cell. The QCM, the counter electrode, and the reference electrode are positioned to be at least partially immersed in the test sample. The test sample may be a drinking water sample.

At 418, the EQCM cell containing the test sample is stabilized. The EQCM cell may be stabilized by leaving the EQCM sample undisturbed. The EQCM cell may be stabilized for, e.g., 300s.

At 420, an electric potential is applied to the QCM. The electric potential may be applied across the counter electrode and a working electrode of the QCM. The electric potential may be applied using the reference electrode as a reference. In some embodiments electric potential may be applied at a voltage of 1.2 V. The electric potential may be applied at a voltage determined previously using cyclic voltammetry. The electric potential may be applied across two electrodes of the QCM as an alternating voltage.

At 422, signals from the EQCM cell are measured and recorded. The signals may include a frequency of the voltage applied across two electrodes of the QCM. The signals may include a change in the frequency. The signals may include a current of the voltage applied across the counter electrode and the working electrode of the QCM.

At 424, the concentration of an analyte is determined. The analyte may be $Mn^{2+}$. Different methods of determining the concentration of Mn are contemplated and may include, but are not limited to, determining a total charge transferred; comparing a total charge transferred to a calibration curve; determining a $\Delta f$ of the QCM; comparing the $\Delta f$ to a calibration curve; obtaining a calibration curve for total charge; and/or obtaining a calibration curve for $\Delta f$.

In some embodiments the method 400 may further include positioning the EQCM cell within a Faraday cage, which may reduce electrical interference when the signals from the EQCM are measured and recorded.

Figure 12:
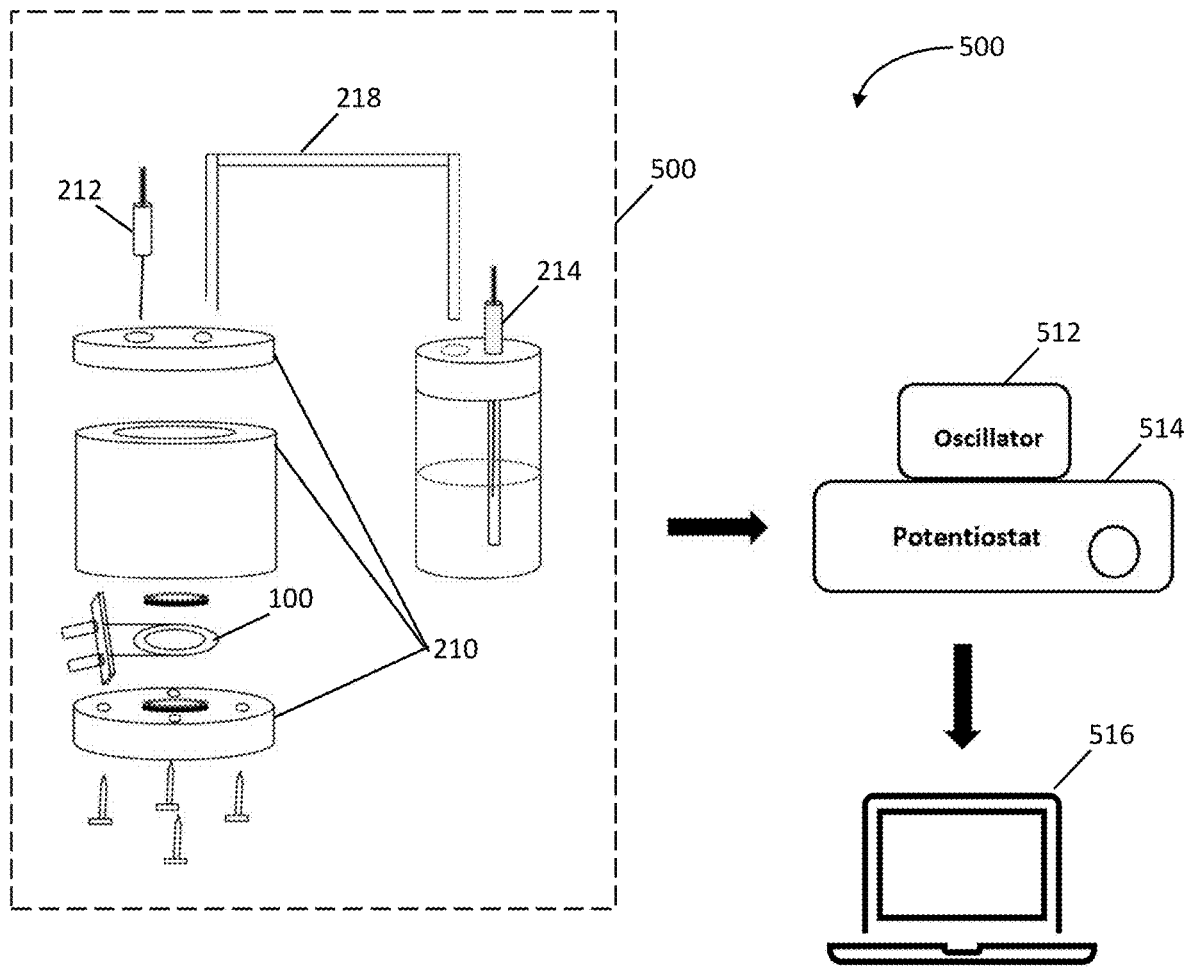
FIG. 12 is a schematic diagram of a system for analyzing water using CA and QCM, according to an embodiment.

FIG. 12 is a schematic diagram of a system 500 for analyzing water using CA and QCM, according to an embodiment. The system 500 includes an EQCM cell 510, oscillator 512, potentiostat 514, and recording device 516. The EQCM cell 500 includes a QCM crystal 100, a container 210, a counter electrode 212, a reference electrode 214, and a salt bridge 218. The EQCM cell 510 may be similar in at least some ways to EQCM cell 200 of FIG. 2, and may be substantively similar to EQCM cell 200.

The QCM crystal 100, the counter electrode 212 and the reference electrode 214 are electronically coupled to the oscillator 512 and the potentiostat 514 to perform CA and QCM measurements. The oscillator 512 and the potentiostat 514 are electronically coupled to the recording device 516 to record the results of CA and QCM measurements. The recording device 516 may be a general purpose computer or an application-specific electronic device.

An implementation of an apparatus for measuring the concentration of an analyte in water at least partially automatically, or fully automatically, will now be described with reference to the embodiment shown in the schematic diagram of FIG. 13A. Of course, other configurations and implementations may be used, as would be apparent to one of ordinary skill in the art.

Figure 13A:
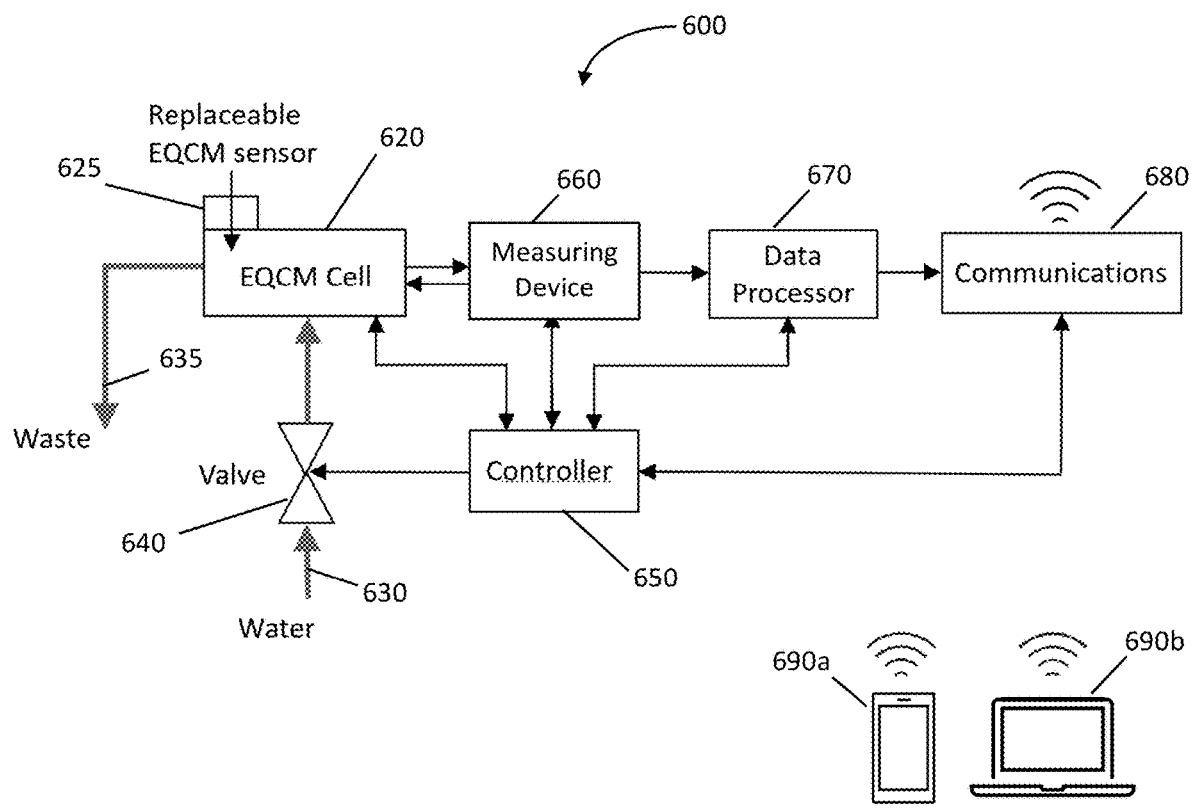
FIGS. 13A and 13B are schematic diagrams of an apparatus for analyzing water, and an implementation in a water distribution system, according to embodiments.
Figure 13B:
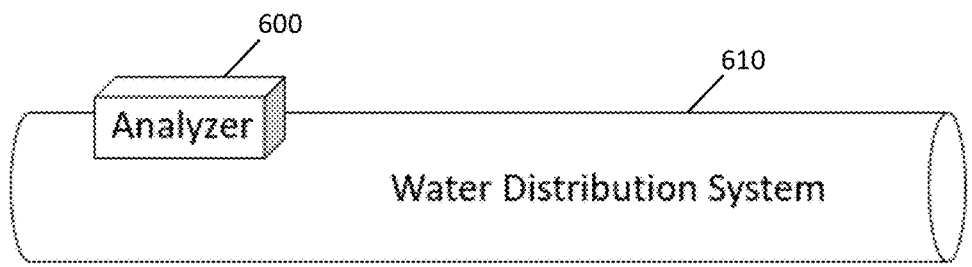

According to embodiments, the apparatus, referred to as an analyzer 600, may be configured as a stand-alone unit, e.g., for table-top use, or in a configuration adapted to be installed on or in proximity to a conduit 610 of a water distribution system, as shown in FIG. 13B, such that water samples can readily be obtained from the conduit. The water distribution system may be residential, commercial, etc.

Referring to FIG. 13A, the analyzer 600 may include components such as an EQCM cell 620 for carrying out CA and QCM measurements. The EQCM cell 620 may have a user-replaceable EQCM sensor 625 that includes an QCM crystal. The EQCM cell may have a water inlet for receiving water to be analyzed and an outlet 635 to discharge "waste" water after analysis. The inlet may be connected to the water distribution system via a valve 640.

The valve 640 may be configured to provide a set amount of water, i.e., a water sample, to the EQCM cell at a time. For example, in the embodiment of FIG. 13A, the valve is actuated by a controller 650. Upon receiving a command signal to begin a measurement, the controller 650 provides a control signal that opens the valve 650, allowing water to flow into the EQCM cell 620. In one embodiment a sensor in the EQCM cell 620 determines when the correct volume of water sample has been reached, and provides a control signal to the controller 650, which then closes the valve 640. The EQCM cell 620 may also be equipped with a discharge valve (not shown in FIG. 13A). In such an embodiment the controller 650 may receive a command (e.g., from the data processor) indicating that a measurement has been completed, and then send a control signal to open the discharge valve to discharge the water sample.

The analyzer may also include a measuring device 660 that performs CA-QCM measurements. The measurement device may apply one or more electrical potentials to one or more electrodes of the EQCM cell 620, and measure and record one or more electrical parameters from the one or more electrodes. In some embodiments the measuring device 660 may be implemented with a potentiostat. The measuring device 660 may implement a measurement procedure in which steps including applying the one or more electrical potentials to the one or more electrodes of the EQCM cell, and measuring and recording one or more parameters from the one or more electrodes are carried out substantially automatically. This may be implemented by executing a control algorithm in a processor (e.g., a microcontroller unit (MCU), firmware, etc.) of the measuring device 660 or in the controller 650. The measuring device may communicate with the controller 650, for example, upon closing the valve 640 and the correct water sample volume attained in the EQCM cell 620, the controller may send a control signal to the measuring device 660 to begin a measurement procedure.

The analyzer 600 may also include a data processor 670 such as a computer, MCU, memory device, etc., that receives measurement data from the measuring device 660 and executes an algorithm that calculates a concentration of one or more analytes, such as Mn, in the water sample. The algorithm, which may be implemented in computer code stored in a non-volatile memory of the data processor, may include performing calculations such as one or more of equations (1) to (4) referred to above. The memory may store a calibration curve or associated data used to determine the concentration of an analyte such as Mn from the CA-QCM measurements. The data processor may communication with the controller, for example, the data processor may send a control signal to the controller indicating that a calculation of an analyte concentration in a water sample has been completed.

The analyzer 600 may also include a communications device 680 that enables communications between the analyzer and at least one other device, referred to herein as a base station, over a network. The communications be over a wired or wireless network. Wireless communications with the at least one other device may be implemented with Bluetooth® (e.g., Bluetooth Low-Energy (BLE)) technology, WiFi, 3G/4G/5G/long term evolution (LTE), etc. The base station may be a smart phone 690a, remote computer 690b, server, etc. The communications device may send a data packet relating to a measured analyte concentration in a water sample to the at least one other device. The communications may be encrypted with, e.g., secure sockets layer (SSL), transport layer security (TLS), or other technology for security. In one embodiment communications may include sending an alarm if the measured concentration is above a threshold. The communications device may receive instructions from the base station, such as an instruction to begin a measurement procedure. In some embodiments, communications received by the base station, such as measured concentration of the analyte, an alarm, etc., may be displayed as an alert on the base station, such as a text message (e.g., SMS), email, or other notification method or real-time alert compatible with the base station. The base station may implement a software application (i.e., an "APP") optionally having a graphical user interface (GUI) that displays and stores data, values of concentrations of an analyte, communications, etc., received from the communications device.

The analyzer may also include a controller 650 that receives signals from, and/or sends control signals to, one or more of the valve 640, the EQCM cell 620, the measuring device 660, the data processor 670, and the communications device 680. The controller may include logic circuitry that performs functions including determining an appropriate control signal to send to the one or more devices based on a received signal corresponding to a command, status of a device, etc. The logic circuitry may be implemented with a processing device such as an MCU, wherein the processing device executes a control algorithm stored in non-volatile memory.

The analyzer 600 may also include a power supply (not shown in FIG. 13A) that provides power to the devices. The power supply may be connected to the mains power, and may have a battery back-up. For remote installations the power supply may include a rechargeable battery optionally with charging provided by a renewable source, e.g., solar (e.g., photovoltaic), wind power generation, etc.

The invention is further described by way of the following non-limiting examples.

EXAMPLES

Chemicals and Reagents

In select embodiments, sulfuric acid (trace metal grade, 98%), agar (molecular genetics), and potassium nitrate (99%) were purchased from Thermo Fisher Scientific. Humic acid (technical), copper(II) sulfate (trace metal basis, 99.999%), iron(III) nitrate nonahydrate (trace metal basis, ≥99.95%), manganese sulfate monohydrate (ReagentPlus, ≥99%), iron(II) sulfate heptahydrate (ReagentPlus, ≥99%), sodium sulfate (anhydrous, 99%) were purchased from Sigma-Aldrich. Milli-Q water with a resistivity of 18.2 MΩ·cm passed through a 0.22 μm filter were used.

In select embodiments, samples were prepared in Milli-Q water and all the Mn samples were prepared by $MnSO_4$. A 10-mL centrifuge tube was used to prepare 0.00200 M Mn stock solution. Then the 0.00200 M Mn stock solution was series diluted by 10-mL or 50-mL centrifuge tubes for desired Mn concentration. The interference study was carried out in sample solution containing 50.0 μM Mn. Various interference agents were dissolved in 50.0 μM Mn solution to prepare different sample mixtures.

In select embodiments, bare QCM quartz crystals with Au thin film electrodes were used. The cleaning strategy used in embodiments described herein to clean the electrode before, between, and after each measurement was 300 s CA at −1.0 V (referred to herein as acid cleaning).

In select embodiments, electrochemical measurements were carried out using a CHI 420C potentiostat (CH Instrument, Texas, USA). The electrochemical cell was placed in a faraday cage for the measurements. The Δf of the QCM quartz crystal (CH Instrument, Texas, USA) were measured simultaneously with the current changes by CA. A quartz crystal was placed in a Teflon QCM cell purchased from CH Instrument (Texas, USA). A platinum wire counter electrode (CH Instrument, Texas, USA) was place in the same cell as the crystal and a Ag/AgCl in 3 M KCl reference electrode (CH Instrument, Texas, USA) was connected to the cell by a homemade 3% Ager 1 M $KNO_3$ salt bridge. Measurements were carried out based on the arrangement shown in FIG. 12 The crystals were first prepared by acid cleaning to make consistent electrode surfaces. A 10-minute waiting time was applied before each Mn deposition procedure to stabilize the initial frequency of the quartz crystal. The Mn film was then deposited by CA at +1.2 V for 300 s on the Au electrode surface of the quartz crystal. An acid cleaning was carried out between each measurement to remove the deposited Mn material.

EQUIVALENTS

Although the disclosure has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the disclosure.

In the preceding description, for purposes of explanation, numerous details are set forth in order to provide a thorough understanding of the embodiments. However, it will be apparent to one skilled in the art that these specific details may not be required. In other instances, well-known structures may be shown in block diagram form in order not to obscure the understanding. For example, specific details are not provided as to whether elements of the embodiments described herein are implemented as a software routine, hardware circuit, firmware, or a combination thereof.

REFERENCES

Berg, K. E.; Adkins, J. A.; Boyle, S. E.; Henry, C. S., Manganese Detection Using Stencil-printed Carbon Ink Electrodes on Transparency Film. Electroanalysis 2016, 28 (4), 679-684.

Health Canada, Guidelines for Canadian Drinking Water Quality: Guideline Technical Document-Manganese. Health Canada: Water and Air Quality Bureau, Healthy Environments and Consumer Safety Branch, Health Canada, Ottawa, Ontario, 2019.

Kang, W.; Rusinek, C.; Bange, A.; Haynes, E.; Heineman, W. R.; Papautsky, I., Determination of manganese by cathodic stripping voltammetry on a microfabricated platinum thin-film electrode. Electroanalysis 2017, 29 (3), 686-695.

Owen, M. P.; Lawrance, G. A.; Donne, S. W., An electrochemical quartz crystal microbalance study into the deposition of manganese dioxide. Electrochimica acta 2007, 52 (14), 4630-4639.

Standard Methods for the Examination of Water and Wastewater, 23rd Edition. American Public Health Association, Water Environment Federation, American Water Works Association, 2017.

Toronto Drinking Water Analysis Summary, 2020 (https://www.toronto.ca/wp-content/uploads/2021/05/8e4a-D521-0106-DrinkingWaterAnalysis2020-AODA.pdf).

World Health Organization, Manganese in Drinking Water—Background document for development of WHO Guidelines for Drinking-water Quality—Version for public review. WHO: World Health Organization, Geneva, Switzerland, 2020.

The invention claimed is:

1. A method for quantifying an analyte in water, comprising:
   exposing a piezoelectric material having at least one electrode disposed thereon to the water;
   electrodepositing the analyte on the electrode by applying an electrical potential to the electrode while simultaneously measuring an electrical current through the electrode as a function of time and a frequency shift of vibration of the piezoelectric material as a function of time;
   using the measured electrical current as a function of time to determine a charge on the electrode and the measured frequency shift as a function of time to determine a mass of the analyte deposited on the electrode; and
   using the charge on the electrode and the mass of the analyte deposited on the electrode to determine a concentration of the analyte in the water.

2. The method of claim 1, wherein the electrical potential applied to the electrode is a stepped voltage.

3. The method of claim 1, wherein the electrical potential applied to the electrode is an alternating voltage.

4. The method of claim 1, wherein the frequency shift of the piezoelectric material is measured as a frequency of a voltage of the piezoelectric material.

5. The method of claim 1, comprising preparing a calibration curve for the analyte, and using the calibration curve to determine the concentration of the analyte in the water.

6. The method of claim 1, comprising cleaning the electrode on the piezoelectric material with an acid prior to electrodepositing the analyte.

7. The method of claim 1, wherein the piezoelectric material comprises a quartz crystal.

8. The method of claim 1, wherein the water is a drinking water sample.

9. The method of claim 1, wherein the analyte is manganese.

10. The method of claim 1, comprising using a processor to execute an algorithm that directs the processor to receive measurement data corresponding to the measured electrical current through the electrode as a function of time and the frequency shift of vibration of the piezoelectric material as a function of time;
    calculate the charge on the electrode and the measured frequency shift as a function of time;
    calculate the mass of the analyte deposited on the electrode;
    use the charge on the electrode and the mass of the analyte deposited on the electrode to calculate the concentration of the analyte in the water; and
    output a value of the concentration of the analyte in the water.

11. Apparatus for quantifying an analyte in water, comprising:
    a cell that is adapted to contain the water;
    a piezoelectric material removably disposed in the cell, the piezoelectric material having at least one electrode disposed thereon, wherein the at least one electrode is exposed to the water when the water is contained in the cell;
    a measuring device that controls electrodepositing the analyte on the electrode by applying an electrical potential to the electrode while simultaneously measuring an electrical current through the electrode as a function of time and a frequency shift of vibration of the piezoelectric material as a function of time;
    a data processing device including a processor that executes an algorithm stored on non-volatile memory, wherein the algorithm directs the processor to:
    receive measurement data from the measuring device corresponding to the measured electrical current through the electrode as a function of time and the frequency shift of vibration of the piezoelectric material as a function of time;
    calculate the charge on the electrode and the measured frequency shift as a function of time;
    calculate the mass of the analyte deposited on the electrode;
    use the charge on the electrode and the mass of the analyte deposited on the electrode to calculate the concentration of the analyte in the water; and
    output a value of the concentration of the analyte in the water;
    the apparatus further comprising a controller that controls operation of the measuring device and the processing device.

12. The apparatus of claim 11, further comprising a communications device that enables the apparatus to communicate with at least one other device over a network;
    wherein the communications include transmitting the value of the concentration of the analyte in the water to the at least one other device.

13. The apparatus of claim 11, wherein the electrical potential applied to the electrode is a stepped voltage.

14. The apparatus of claim 11, wherein the electrical potential applied to the electrode is an alternating voltage.

15. The apparatus of claim 11, wherein the frequency shift of the piezoelectric material is measured as a frequency of a voltage of the piezoelectric material.

16. The apparatus of claim 11, wherein the piezoelectric material comprises a quartz crystal.

17. The apparatus of claim 11, wherein the water is a drinking water sample.

18. The apparatus of claim 11, wherein the analyte is manganese.

19. The apparatus of claim 11, wherein the apparatus calculates the concentration of the analyte in the water; and outputs a value of the concentration of the analyte in the water at least partially automatically.

20. The apparatus of claim 11, wherein the apparatus is configured to obtain a water sample for analysis from a water distribution system.

* * * * *